United States Patent
Olek et al.

(10) Patent No.: US 11,597,975 B2
(45) Date of Patent: Mar. 7, 2023

(54) PDCD1 AS EPIGENETIC MARKER FOR THE IDENTIFICATION OF IMMUNE CELLS, IN PARTICULAR PD1+ CELLS

(71) Applicant: Epiontis GmbH, Berlin (DE)

(72) Inventors: Sven Olek, Berlin (DE); Udo Baron, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 18 days.

(21) Appl. No.: 16/758,131

(22) PCT Filed: Oct. 24, 2018

(86) PCT No.: PCT/EP2018/079184
§ 371 (c)(1),
(2) Date: Apr. 22, 2020

(87) PCT Pub. No.: WO2019/081590
PCT Pub. Date: May 2, 2019

(65) Prior Publication Data
US 2021/0123100 A1    Apr. 29, 2021

(30) Foreign Application Priority Data
Oct. 25, 2017  (DE) .......................... 102017125019.0

(51) Int. Cl.
*C12Q 1/6881*    (2018.01)

(52) U.S. Cl.
CPC ..... *C12Q 1/6881* (2013.01); *C12Q 2600/154* (2013.01)

(58) Field of Classification Search
None
See application file for complete search history.

(56) References Cited

U.S. PATENT DOCUMENTS

2019/0249258 A1* 8/2019 Dietrich ............... C12Q 1/6886

FOREIGN PATENT DOCUMENTS

| EP | 3029150 A1 | 6/2016 |
| WO | WO 2012/162660 A2 | 11/2012 |
| WO | WO 2017/198617 * | 11/2017 |

OTHER PUBLICATIONS

Raimondi, et al. Journal of Immunology (2006) 176:2808-2816 (Year: 2006).*
Feng (PNAS 2010 vol. 107 No. 19 pp. 8689-8694).*
Antequera and Bird, Number of CpG Islands and Genes in Human and Mouse, Proc Natl Academy of Science USA 90: 11995-9, 1993.
Bally et al., NF-κB regulates PD-1 expression in macrophages, The Journal of Immunology, May 1, 2015; 194(9):4545-54.
Booth, Michael J. et al., Quantitative Sequencing of 5-Methylcytosine and 5-Hydroxymethylcytosine at Single-Base Resolution, Science May 18, 2012, vol. 336, No. 6083, pp. 934-937.
Esteller, M., CpG Island Hypermethylation and tumor Suppressor Genes: a Booming Present, a Brighter Future, Oncogene 21:5427-5440, 2002.
Goltz et al., Promoter methylation of the immune checkpoint receptor RD-1 (PDCD1 is an independent prognostic biomarker for biochemical recurrence-free survival in prostate cancer patients followwing radical prostatectomy, Oncoimmunology, Sep. 2, 2016, 5(10):e1221555.
Jones and Laird, Cancer-Epigenetics Comes of Age, Nature Genetics 21: 163-167, 1999.
Kristensen and Hansen PCR-Based Methods for Detecting Single-Locus DNA Methylation Biomarkers in Cancer Diagnostics, Prognostics, and Response to Treatment, Clinical Chemistry 55:8 1471-1483 (2009).
Laird, Peter W., The Power and the Promise of DNA Methylation Markers, Nature Reviews Cancer 3, pp. 253-266 (2003).
Pesce, Silvia et al, Identification of a subset of human natural killer cells expressing high levels of programmed death 1: A phenotypic and functional characterizationnn, Journal of Allergy and Clinical Immunology, vol. 139, No. 1,May 27, 2016, p. 335.
Raimondi, G. et al., Regulated Compartmentalizatio of Programmed Cell Death-1 Discriminates CD4+CD25+ Resting Regulatory T Cells From Activated T Cells, The Journal of Immunology, vol. 176, No. 5, Feb. 21, 2006, pp. 2808-2816.
Youngblood et al., Chronic virus infection enforces demethylation of the locus that encodes PD-1 in antigen-specific CD8 T cells, ,Sep. 23, 2011; 35(3): 400-412.

* cited by examiner

*Primary Examiner* — Amanda Haney

(57) ABSTRACT

The present invention relates to a method, in particular an in vitro method, for identifying PD1+ cells, comprising analyzing the methylation status of at least one CpG position in the mammalian gene region for Programmed cell death 1 (PDCD1), wherein a demethylation or lack of methylation of said gene region is indicative for a PD1+ cell, when compared to a non-PD1+ cell. The analyses according to the invention can identify PD1+ cells on an epigenetic level and distinguish them from all other cells in complex samples, such as, for example, other blood or immune cells. The present invention furthermore provides an improved method for quantifying PD1+ cells, in particular in complex samples. The method can be performed without a step of purifying and/or enriching cells, preferably in whole blood and/or non-trypsinized tissue.

Figure 1:
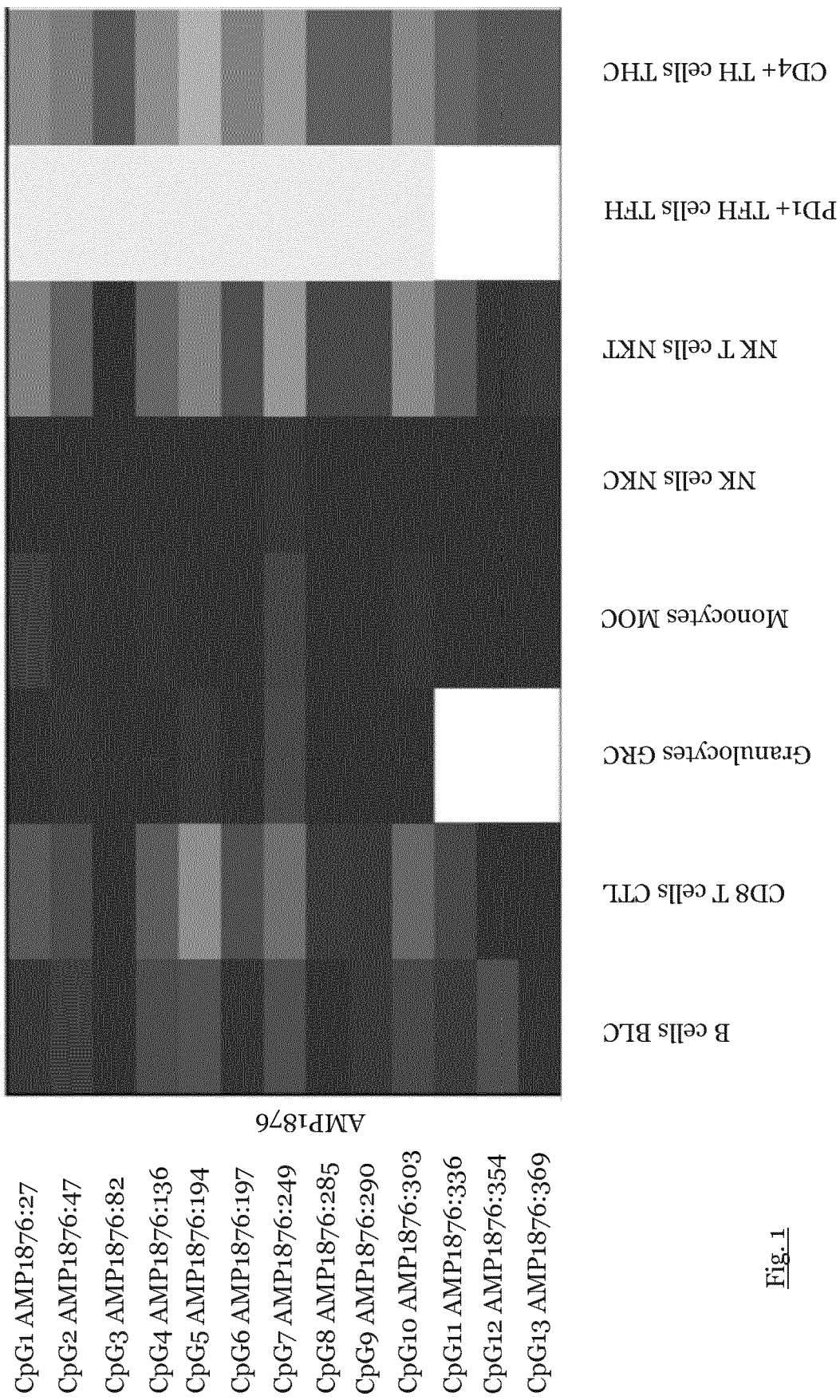
Figure 1:
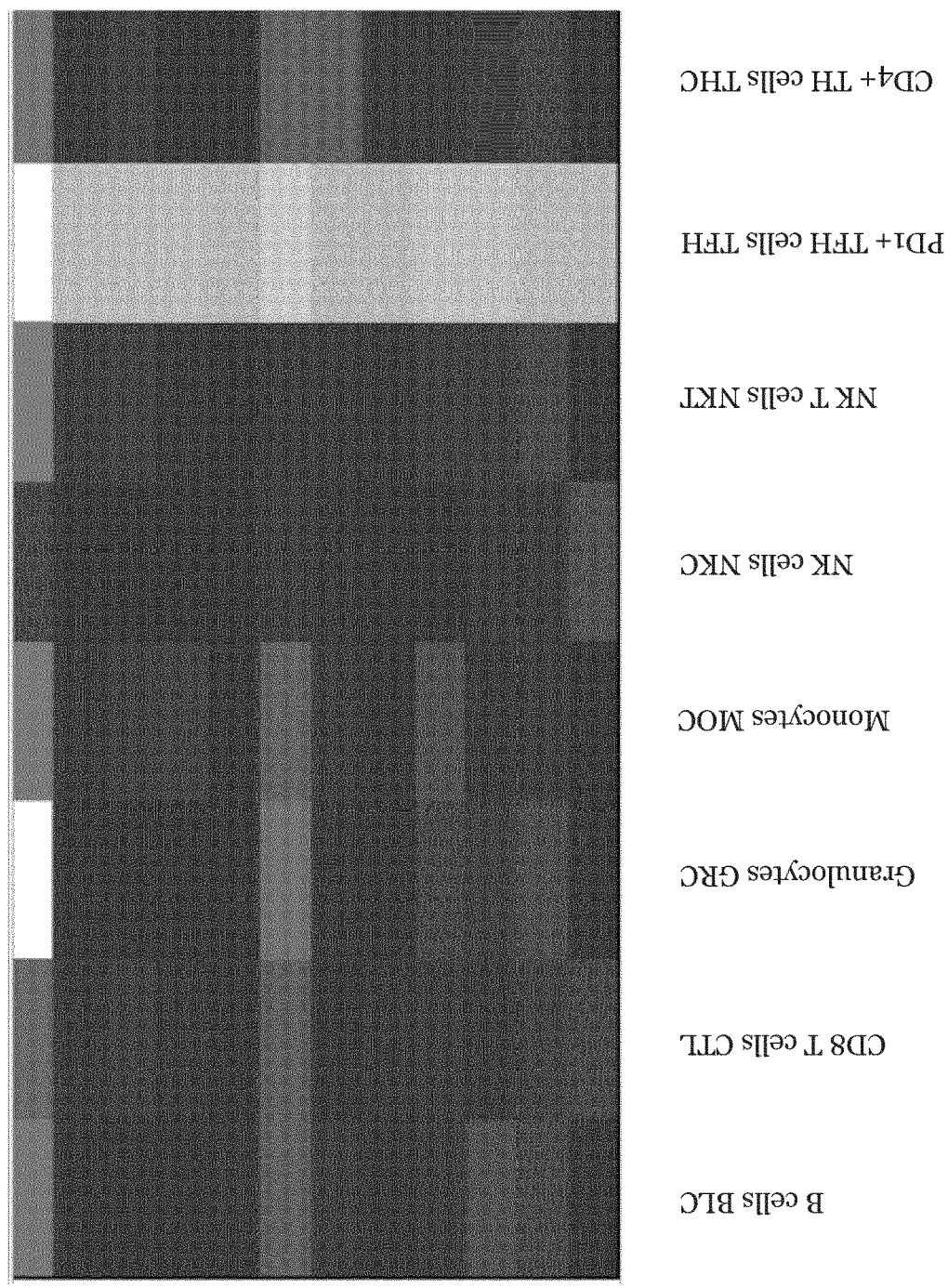
Figure 1:
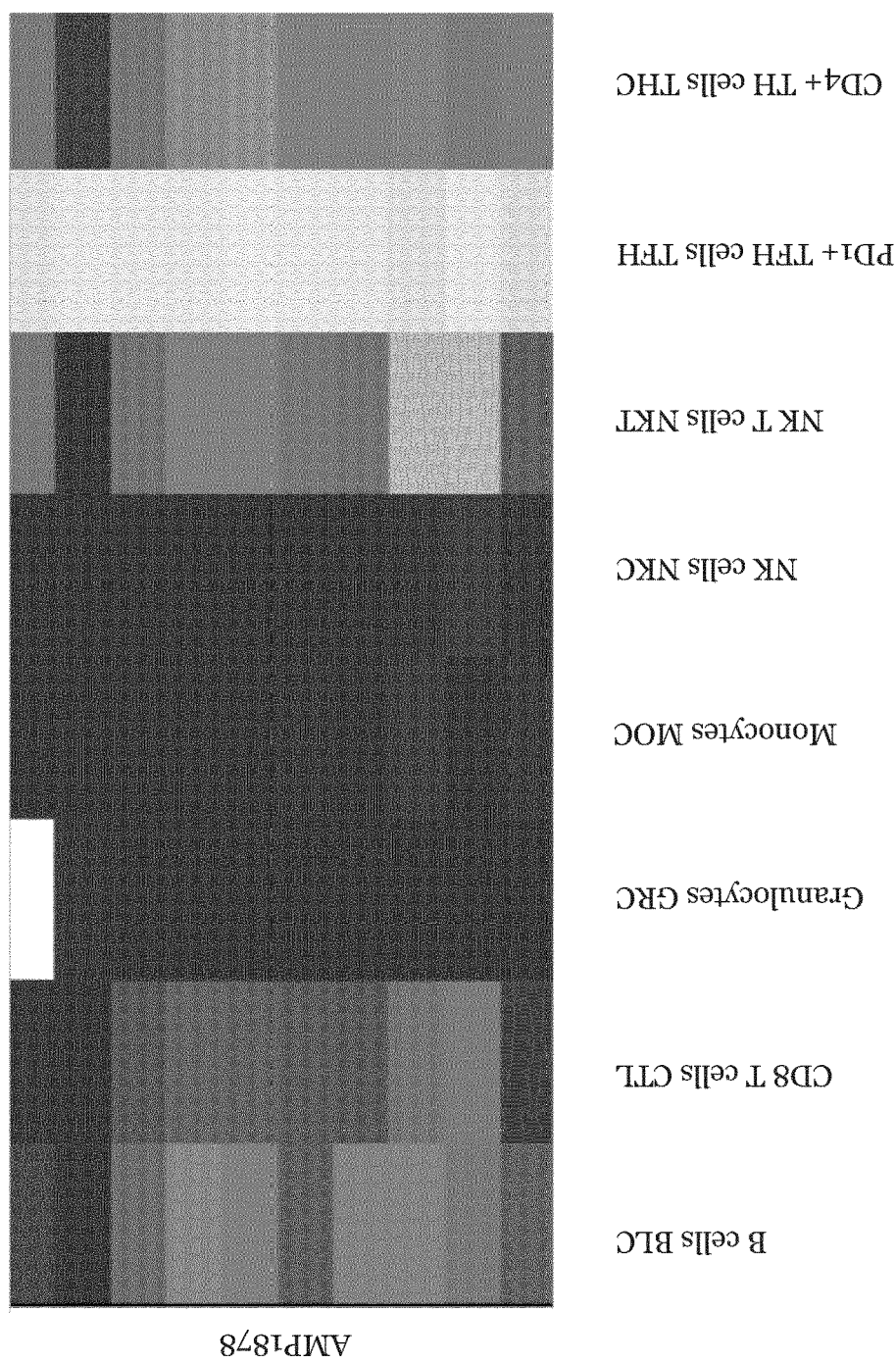

11 Claims, 8 Drawing Sheets
Specification includes a Sequence Listing.

agtagcaatgtggagagaccatcaggcagccctggcctcagtggccgcagtcccctggctccacgctgggcccac
cccaccaggtctcctctcccatggcccaggggccttcagtgggactgagaggaggagggaaggagagtgggtgac
agggaagaactgcagggagagaggagagggtgggagaaggagaaggaaggaaggggtaggatggaagctgggtt
tctccctgtgcccgcccctactccaggacatgtgtccaagccctggcaggtggaattttgggggcagggccttg
gtggtgaggagaccttccagggtctgatagcatctcccatctcagagcccacctcctgggcccagcctccctc
cagcccacacagtggcattcccagtcctcagaggacagcttcgtcccacaaagctcagagccttgaggaaggccc
actgctgccctggaacagagacagcattcaacagaggttggaacaaggctctacagggctgggggcagagggagg
ttctgtccagaatctgccttcaggacaagtacagccagcaggggcagcttagccacttatccactgcctgggcga
ggcacagggctatggaggcacctaccaaccaacagttctccagccccagagcccagcccctgaggcacaagggt
gggtgtgccaggagacagttgctgcgggccaccttagctgtctggcagcacagtgggtgctgccaggctccctgg
gggcccccgccaagcccacctggccagctgggccccccccacctccccaccaagccacccacacagcctcaca
tctctgagacccgggagtggccctttgttcataaacgagagcttcctcgccgtggccgcgcctcgcagacatcat
ctttgatgctcttttttccactgtttcggtgctttaatgttttcccttcagagccgggccgagtgtctctcggagc
caggcagccgcgccagctgtcaggcggtttctagcctcgcttcggttatttaagctgatgagcctgacgcatct
catcactaatatcagcagtttcatttctcctgttttccattcgctgtaataaaatgctcagcacagaatacaagg
agataagcaagccatttcacaaacgccgggccgccagccaggcccaggcactggaccccctgaaccaccccaccc
tggcacgagtgggctggagggcagggccccgggaagaaggtcaaggctggaaggggaggtcagcctcacagcca
gcccctgccaccgccccagccccccgtcaggctgttgcaggcatcacacggtggaaagatctggaactgtggcc
atggtgtgaggccatccacaaggtggaagctttgaggggagccgattagccatggacagttgtcattcagtagg
gtcacctgtgcccagcgaaggggatgggccgggaaggcagaggccaggcacctgccccagcaggggcagagg
ctgtgggcagccgggaggctcccagaggctccgacagaatgggagtgggtgagcccacccctcactgcagccc
aggaacctgagcccagaggggccaccaccttccccaggcagggaggcccggcccccagggagatggggggat
ggggaggagaagggcctgcccccacccggcagcctcaggagggcagctcgggcgggatatggaaagaggccac
agcagtgagcagagacacagaggaggaagggccctgagctggggagacccccacggggtagggcgtggggcca
cgggcccacctcctccccatctcctctgtctccctgtctctgtctctctctccctcccccaccctctcccccagtc
ctaccccctcctcaccctcctccccagcactgcctctgtcactctcgcccacgtggatgtggaggaagagggg
gcgggagcaaggggcgggcaccctccccttcaacctgacctgggacagtttcccttccgctcacctccgcctgagc
agtggagaaggcggcactctggtggggctgctccaggcatgcagatcccacaggcgccctggccagtcgtctggg
cggtgctacaactgggctggcggccaggatggttcttaggtaggtggggtcggcggtcaggtgtcccagagccag
gggtctggagggaccttccaccctcagtccctggcaggtcgggggtgctgaggcgggcctggccctggcagccc
aggggtcccggagcgagggtctggagggacctttcactctcagtccctggcaggtcgggggtgctgtggcagg
cccagccttggccccagctctgccccttaccctgagctgtgtggctttgggcagctcgaactcctggttcctc
tctgggcccaactcctcccctggcccaagtcccctctttgctcctgggcaggcaggacctctgtcccctctcag
ccggtccttggggctgcgtgtttctgtagaatgacgggtcaggctggccagaaccccaaaccttggccgtgggga
gtctgcgtggcggctctgccttgcccaggcatccttggtcctcactcgagttttcctaaggatgggatgagccc
atgtgggactaaccttggctttacgacgtcaaagtttagatgagctggtgatattttctcattatatccaaagt
gtacctgttcgagtgaggacagttcttctgtctccaggatccctcctgggtggggattgtgcccgcctgggtctc
tgcccagattccagggctctccccgagccctgttcagaccatccgtgggggaggccttggcctcactctcccgga
tcgaggagagagggagcctcttcctgggctgcccgtgaccctgggccctctgtgtacactgtgaccacagcccgc
tcctggaccctctgtgcccggctggccctctgtgccagccagcctgcacctggggatgccaaggcctggggagg
gtggtttcacccaggccaagcctaagacagtccctctgggccctgctgggtaccggggtgtgacaccactgggag
gacaagatgaggggcacccctggggccgccctgacacccct$_{cg}$aggctcctgccc$_{cg}$gggtcctggtgccccctt
cactgtggcagg$_{cg}$actggggttccccacct$_{cg}$gcccctctcc$_{cg}$gggcctgctcccggcacctgaggcagcatc
cttgtcagggc$_{cg}$tgccttcctgcctcag$_{cg}$ccacctcttaaggttggcc$_{cg}$tgggtcactcaggactcagaactgg
agattctgggcaaaaggcaaagagcaaagggccaaaaggcatcccaggagacgactgcgggggaaccagagggc
agaggggcgctcgtcacaggggagggggagctgagcgaggcaggaggggagccgagcctctcccccgtgtcccg
gctcttcaggcacgccctcgggacgccaccctccccgacccaggcggggaaagataagagcaaggtgtccgcagcc
tgacactcgtgcctcaggtgcccgcgcttgtgccggacaagactctcacaggtggcatgcctcggtttccccact
ggtaacagcacagggcactcagcaaggcgcagtgggcatgactgggggtcctgtgggtcctgacccagatgtggcc
accccggccgcagtggtcttcattccaggatgcctctttttcctcctgatctattcactgcgttcgccattcggt
cattcccggggccaccactcccacctcaggtgtgtgcttcccttgtgttttatgagatatcccaacccggctgc
ttattggccccgtccgagggcaggagcataaataagagcctctgctttggcgtgggaccactgtgagctccagtc
agcgctgccactgctgagctctgggccttcgacaggacttggccccttactgacttctccgtgtgctttgggtca
tgggtgaggacgcctcctggcaaggctgcgtcctgaggattaaatcgggtcatctgtgaaaactaccagcccag

Fig. 3 a cccctgacactttttttgtttgtttcttttagtgacagggtcttgctctgtcacccaggctggagtgcagtggtgt
gatctcggctcactcgacctccggggctcaagcaattctcccacctctgcctccagagtagctgggactataggc
acgtgccaccctgccaggctaatttcttccattttttttagagacagggtctcgctatgttccccaggctgggct
caaatggtcctcccacctcagcctccccaagtactgggattacaggcataagccactgcatctggcctccatgac
acatatttttaaagtctgattttttaaagtcaaacttttgaagtcagatttttaaacggactattttgaaaaatata
caaaaacgtttaaaaacaatgaatatccctcacctagaatcaataactaagaatattgacacatttgctttgggg
actgggcggctggagctgccatgacaaagctccgccgaccgagtggcttttaaacagagcctgccctctcgccga
ctgagggctggacgtgcaggatggagctccgcagggtcggctcccctgtgctctgaggggctctgctcagcctct
cccggctgtggcttaaaaacagagcctgtcctcccgccgtggggggctggacatgcaggaccgaggggccacagg
gtcggctccctgtgctccgagagggctctgctcagcttctcctggctgggggttttgtggccaccctctgtgtt
cctgggttcagaagcatccccaggctctgccttcatctgcacgggtgactctgtacaggaagccaggcctgc
tggtcaatggccacccagccctgtgccctcatcttacctagtcccagctgccgtcacctattcctaataaggcc
gccttctgaggtcatgggttaggacttccacataggaatctgtggggacacggttcggcccacagccctccca
cctccacacacacacgactgtgaggagttggaagacctcactcctcacccctgccaggtcctctagggacaag
ctcgctgtcctcatcccagcacagcccgtgggacggttccttgtccctaatgggaccacggtcagagatgccgg
gtctggtctgggccagcaggttcctccgcccggggcaggcagccttcttctgtgcgcttctggaaagcaatgtcc
tgtaatgcggtctctctgcgggagcaccccaccgccacctcacaggcctgttccacagcccgggatgggctct
gtctccctcctgacctgcatagggcacagccctctctcatcaacccacgatcctacgtggatccgagagggagc
acctggggaaacaatggaatcccatagaaacaccccaaatctaacttgatccaggaccagccagtggtcacttct
gaatattcaccttcctagtagacactaccagccaagggaggccaggaagccttcctggaggaggtggcctgagga
ctggggtgaggcaggccctgcgtgggggtcgccacccagcaccccacactgggtgggagccagtctctgagact
ggctggggaggtgggagagggggctgcttgaactgcagacaccgaggtctagccccacccacccagccagtt
ggtggaggcaggggaggccgaggggcccagctggacctgctccccggggtggattccaaaatagggggttgggg
ggggcggaacaggagcccagggtcctggcttgaggcccagtggctgagggctggtgcaagccagacaggaaaagg
gttgagcctgtcagcgccagcacagatcaagtcaggagcaggtccctccaccaatgtgtgcaaataaatagcagc
taagtttccagttacaagaacaatgcacagatggtcccagggacattg$_{cg}$gtgtggacacacag$_{cg}$gccattgtcc
tgt$_{cg}$ccagcacct$_{cg}$ccctacagctgggggtcccttagcacttcctagccatgcagggtccctgctcacagtac
c$_{cg}$tgatgacttctgttcctcacctgcctgtctgtcccgacagctgcatggcagccctggcctgggagatggagac
cc$_{cg}$aggggctgcctg$_{cg}$gtggtggggcccctgggtccccactgcattcccagaaacccagagggcagggcatttc
ccctgctctgtgc$_{cg}$agtccacccagccccagcctaggcccagtaagggctgcagcccaccctgtcccaggctgcc
tcccaggagccctcttggccctgatgccagaagcccatcttcctccattcaggcaggtctctgagtgccctggcc
tggctgcctgctggccctgagagtcacactaccccacagccctccttggtcaaaatccactctggagtggctgga
agattccccgggcccacgccgcacacgccatgcagggagcttcccctggccggccggcagacaagggcggtctc
agagaggggctcacctcagcagcccttgtgtagctggccctcgccctgccacctctgggaacaccaccagga
agctggggacaggcacgcaggtgaaggaggcgagcgcttgtcagccgggaggccatgggcacagagggaacagg
gacaccctgggtggcctcaaggtcacttcaaacccctcactcgtccctggggagggtgcccagtgaggttggcac
taggagttggtcctggtcacatgacagacccacccacctctggtgtccagccagcacgccgtgggccagcctggc
tgcagggacacgagggcagcagcccctcctcctctgagctggttgctccttgagtcatcaccaccgcctgccac
ggaggccgcctgtcccaggaagcagagggaccgcagctgtggcaaccagggcctggtctctgtgtcacctcgctg
gggggccgtgcccaggcctgagacggaactgagtgacagtgcactgggtctgacagtgtggggctggcgccatgt
ttggggaaccctgtggcatgggacctgtgggtgagccgggaaaatcaccccgttgcatggcatctcgggcctgga
tcttaagcgcctgtgttggtgcctccgcctggcggaagagccgcgaccccacgttgccatgcgggtatcccaag
ccctgaccctggcaggcatatgtttcaggaggtccttgtcttgggagcccagggtcggggcccgtgtctgtcc
acatccgagtcaatggcccatctcgtctctgaagcatctttgctgtgagctctagtccccactgtcttgctggaa
aatgtggaggccccactgccactgccagggcagcaatgcccataccacgtggtcccagctccgagcttgtcct
gaaaaggggcaaagactggaccctgagcctgccaaggggccacactcctcccagggctggggtctccatgggca
gcccccacccacccagaccagttacactcccctgtgccagagcagtgcagacaggaccaggccaggatgcccaa
gggtcaggggctggggatgggtagccccaaacagccctttctggggggaactggcctcaacggggaaggggtga
aggctcttagtaggaaatcagggagacccaagtcagagccaggtgctgtgcagaagctgcagcctcacgtagaag
gaagaggctctgcagtggaggccagtgcccatccccgggtggcagaggcccagcagagacttctcaatgacatt
ccagctgggtggcccttccagagcccttgctgcccgagggatgtgagcaggtggccggggaggctttgtggggc
cacccagcccctcctcacctctctccatctctcagactcccagacaggccctggaaccccccaccttctccc
cagccctgctcgtggtgaccgaaggggacaacgccaccttcacctgcagcttctccaacacatcggagagcttcg
tgctaaactggtaccgcatgagccccagcaaccagacggacaagctggccgccttccccgaggaccgcagccagc
ccggccaggactgccgcttccgtgtcacacaactgcccaacgggcgtgacttccacatgagcgtggtcagggccc
ggcgcaatgacagcggcacctacctctgtggggccatctccctggcccccaaggcgcagatcaaagagagcctgc
gggcagagctcagggtgacaggtgcggcctcggaggccccggggcaggggtgagctgagccggtcctgggtggg

Fig. 3 b

```
tgtcccctcctgcacaggatcaggagctccagggtcgtagggcagggaccccccagctccagtccagggctctgt
cctgcacctggggaatggtgaccggcatctctgtcctctagctctggaagcaccccagcccctctagtctgccct
caccccctgaccctgaccctccaccctgacccccgtcctaaccccctgacctttgtgcccttccagagagaagggcag
aagtgcccacagcccaccccagcccctcacccaggccagccggccagttccaaaccctggtggttggtgtcgtgg
gcggcctgctgggcagcctggtgctgctagtctgggtcctggccgtcatctgctcccgggccgcacgaggtaacg
tcatcccagcccctcggcctgccctgccctaaccctgctggcggccctcactcccgcctccccttcctccaccct
tccctcaccccaccccacctcccccatctccccgccaggctaagtccctgatgaaggccctggactaagaccc
ccccacctaggagcacggctcagggtcggcctggtgaccccaagtgtgtttctctgcagggacaataggagccag
gcgcaccggccagcccctggtgagtctcactcttttcctgcatgatccactgtgccttccttcctgggtgggcag
aggtggaaggacaggctgggaccacacggcctgcaggactcacattctattatagccaggaccccacctccccag
cccccaggcagcaacctcaatccctaaagccatgatctggggccccagcccacctgcggtctccgggggtgcccg
gcccatgtgtgtgcctgcctgcggtctccaggggtgcctggcccacgcgtgtgcccgcctgcggtctctgggggt
gcccggcccacatatgtgcctgcctgcggtctccaggtgtgcccggcccatgcgtgtgcccacctgcgagggcgt
ggggtgggcttggtcatttcttatcttacattggagacaggagagcttgaaaagtcacattttggaatcctaaat
ctgcaagaatgccagggacatttcagaggggggacattgagccagagaggagggggtggtgtcccccagatcacacag
agggcagtggtgggacagctcagggtaagcagctcgtagtgggggggcccaggttcggtgccggtactgcagccag
gctgtggagccgcgggcctccttcctgcggtgggccgtgggctgactccctctcccttctcctcaaagaagga
ggacccctcagccgtgcctgtgttctctgtggactatggggagctggatttccagtggcgagagaagaccccgga
gccccccgtgccctgtgtccctgagcagacggagtatgccaccattgtctttcctagcggaatgggcacctcatc
ccccgcccgcaggggctcagccgacggccctcggagtgcccagccactgaggcctgaggatggacactgctcttg
gcccctctgaccggcttccttggccaccagtgttctgcagaccctccaccatgagcccgggtcagcgcatttcct
caggagaagcaggcagggtgcaggccattgcaggccgtccaggggctgagctgcctgggggcgaccggggctcca
gcctgcacctgcaccaggcacagccccaccacaggactcatgtctcaatgcccacagtgagcccaggcagcaggt
gtcaccgtcccctacaggagggccagatgcagtcactgcttcaggtcctgccagcacagagctgcctgcgtcca
gctccctgaatctctgctgctgctgctgctgctgctgctgcctgcggcccggggctgaaggcgccgtggccc
tgcctgacgccccggagcctcctgcctgaacttgggggctggttggagatggccttggagcagccaaggtgcccc
tggcagtggcatcccgaaacgccctggacgcagggcccaagactgggcacaggagtggggaggtacatgggctgg
ggactccccaggagttatctgctccctgcaggcctagagaagtttcagggaaggtcagaagagctcctggctgtg
gtgggcagggcaggaaaccctccaccttacacatgcccaggcagcacctcaggccctttgtggggcagggaag
ctgaggcagtaagcgggcaggcagagctggaggcctttcaggcccagccagcactctggcctcctgccgccgcat
tccaccccagcccctcacaccactcgggagagggacatcctacggtcccaaggtcaggagggcagggctggggtt
gactcaggcccctcccagctgtggccacctgggtgttgggagggcagaagtgcaggcacctagggcccccatgt
gcccaccctgggagctctccttggaacccattcctgaaattatttaaagggggttggccgggctcccaccagggcc
tgggtgggaaggtacaggcgttcccccggggcctagtaccccgccgtggcctatccactcctcacatccacaca
ctgcaccccactcctggggcagggccaccagcatccaggcggccagcaggcacctgagtggctgggacaaggga
tccccccttcctgtggttctattatattataattataattaaatatgagagcatgctaaggagttctgtcctgtc
tggtggctgtgggggcagtgggcaggagggagggaggcctccagggagggacaaggcggcagccaggctgaggct
gtgtgtggagggtgctggtggctcccctggatcctggcctgagtcaggccttcccctcgctgtcccagaaacaca
caggccctcctcgccctgtttgccccactcacatgtagagccctccggtgaaaaattcctccaacatcacggggc
tggggacaccatcttccccaagcccaggccttttaggggggtcccacggcccctggccccaggcttcctggcca
ggcatgggtgtccctgagtgactgtgcctgctccatagccccgtgtccccatgcctaccagtccctccgggcag
gggtggtacctggtgccagggcgtccacagcggggtggagggctgccctggctatgagggacacagcatctgc
gggtccctccccaagtacacagggtggggcagcggggaggcggggtcacgtctgctggagccctatcaccctg
ctgcggtccttggcagctagcagcagggacggtgcagggaaaggagcctgccaggccctcgggcaccgcagcca
aacaccactgacaccccggggctcattctctgcttgccatcctg
```

Fig. 3 c

SEQUENCE LISTING

```
<160> NUMBER OF SEQ ID NOS: 13

<210> SEQ ID NO 1
<211> LENGTH: 11680
<212> TYPE: DNA
<213> ORGANISM: Homo sapiens

<400> SEQUENCE: 1
agtagcaatg tggagagacc atcaggcagc cctggcctca gtggccgcag tccoctggct      60 ccacgctggg cccaccccac caggtctcct ctcccatggc caggggcct tcagtgggac      120 tgagaggagg agggaaggag agtgggtgac agggaagaac tgcagggaga gaggagaggg      180
gtgggagaag gagaaggaag gaaggggtag gatggaagct gggtttctcc ctgtgcccgc      240
cccctactcc aggacatgtg tccaagccct ggcaggtgga attttggggg cagggccttg      300
gtggtgagga gaccttccag gggtctgata gcatctccca tctcagagcc cacctcctgg      360
gcccagcctc cctccagcc cacacagtgg cattcccagt cctcagagga cagcttcgtc      420
ccacaaagct cagagccttg aggaaggccc actgctgccc tggaacagag acagcattca      480
```

```
acagaggttg gaacaaggct ctacagggct gggggcagag ggaggttctg tccagaatct    540
gccttcagga caagtacagc cagcaggggc agcttagcca cttatccact gcctgggcga    600
ggcacagggc tatggaggca cctaccaacc aacagttctc cagccccaga gccccagccc    660
ctgaggcaca agggtgggtg tgccaggaga cagttgctgc gggccacctt agctgtctgg    720
cagcacagtg ggtgctgcca ggctccctgg gggcccccg ccaagcccac ctggccagct     780 gggcccccc ccacctcccc accaagccac ccacacagcc tcacatctct gagacccggg     840
agtggccctt tgttcataaa cgagagcttc ctcgccgtgg ccgcgcctcg cagacatcat    900 cttttgatgct ctttttccac tgtttcggtg ctttaatgtt ttcccttcag agccgggccg   960
agtgtctctc ggagccaggc agccgcgcca gctgtcaggc ggtttctagc ctcgcttcgg    1020
ttattttaag ctgatgagcc tgacgcatct catcactaat atcagcagtt tcatttctcc    1080
tgttttccat tcgctgtaat aaaatgctca gcacagaata caaggagata agcaagccat    1140
ttcacaaacg ccgggccgcc agccaggccc aggcactgga ccccctgaac caccccaccc    1200
tggcacgagt gggctggagg gcagggcccc ggggaagaag gtcaaggctg aaggggagg    1260 tcagcctcac agccagcccc tgccaccgcc ccagccccc cgtcaggctg ttgcaggcat     1320
cacacggtgg aaagatctgg aactgtggcc atggtgtgag gccatccaca aggtggaagc    1380
tttgaggggg agccgattag ccatggacag ttgtcattca gtagggtcac ctgtgcccca    1440
gcgaaggggg atgggccggg aaggcagagg ccaggcacct gccccccagca ggggcagagg   1500 ctgtgggcag ccgggaggct cccagaggct ccgacagaat gggagtgggg ttgagcccac    1560
ccctcactgc agcccaggaa cctgagccca gaggggccca cccaccttcc ccaggcaggg    1620
aggcccggcc cccagggaga tgggggggat ggggaggag aagggcctgc ccccacccgg     1680
cagcctcagg aggggcagct cggcgggat atggaaagag gccacagcag tgagcagaga    1740
cacagaggag gaaggggccc tgagctgggg agacccccac ggggtagggc gtggggggcca  1800 cgggcccacc tcctccccat ctcctctgtc tccctgtctc tgtctctctc tccctcccc    1860 accctctccc cagtcctacc ccctcctcac ccctcctccc ccagcactgc ctctgtcact   1920
ctcgcccacg tggatgtgga ggaagagggg gcggagcaa ggggcgggca ccctcccttc    1980
aacctgacct gggacagttt cccttccgct cacctccgcc tgagcagtgg agaaggcggc   2040
actctggtgg ggctgctcca ggcatgcaga tcccacaggc gccctggcca gtcgtctggg   2100
cggtgctaca actgggctgg cggccaggat ggttcttagg taggtggggt cggcggtcag   2160
gtgtcccaga gccagggggtc tggagggacc ttccacccctc agtccctggc aggtcggggg  2220
gtgctgaggc gggcctggcc ctggcagccc aggggtcccg gagcgagggg tctggaggga   2280
cctttcactc tcagtccctg gcaggtcggg gggtgctgtg gcaggccag ccttggcccc    2340 cagctctgcc ccttaccctg agctgtgtgg ctttgggcag ctcgaactcc tgggttcctc   2400
tctgggcccc aactcctccc ctggcccaag tccctctttt gctcctgggc aggcaggacc   2460
tctgtcccct ctcagccggt ccttggggct gcgtgtttct gtagaatgac gggtcaggct   2520
ggccagaacc ccaaaccttg gccgtgggga gtctgcgtgg cggctctgcc ttgcccaggc   2580
atccttggtc ctcactcgag ttttcctaag gatgggatga gccccatgtg ggactaacct   2640
tggctttacg acgtcaaagt ttagatgagc tggtgatatt tttctcatta tatccaaagt   2700
gtacctgttc gagtgaggac agttcttctg tctccaggat ccctcctggg tggggattgt   2760
gcccgcctgg gtctctgccc agattccagg gctctccccg agccctgttc agaccatccg   2820
```

-continued

```
tgggggaggc cttggcctca ctctcccgga tcgaggagag agggagcctc ttcctgggct    2880
gcccgtgacc ctgggccctc tgtgtacact gtgaccacag cccgctcctg gaccctctgt    2940
gcccggctgg ccctctgtgc ccagccagcc tgcacctggg gatgccaagg cctggggagg    3000
gtggtttcac ccaggccaag cctaagacag tccctctggg ccctgctggg taccggggtg    3060
tgacaccact gggaggacaa gatgaggggc acccctgggg ccgccctgac accccctcga    3120
ggctcctgcc ccgggggtcc tggtgcccct tcactgtggc aggcgactgg gggttcccca    3180
cctcggcccc tctcccgggg cctgctcccc ggcacctgag gcagcatcct tgtcagggcc    3240
gtgccttcct gcctcagcgc cacctcttaa ggttggcccg tgggtcactc aggactcaga    3300
actggagatt ctgggcaaaa ggcaaagagc aaagggccaa aaggcatccc agggagacga    3360
ctgcggggga accagagggc agaggggcgc tcgtcacagg ggaggggggag ctgagcgagg    3420 caggagggga gccgagcctc tccccccgtg tcccggctct tcaggcacgc cctcgggacg    3480
ccaccctccc cgacccaggc gggaaagata agagcaaggt gtccgcagcc tgacactcgt    3540
gcctcaggtg cccgcgcttg tgccggacaa gactctcaca ggtggcatgc ctcggtttcc    3600
ccactggtaa cagcacaggg cactcagcaa ggcgcagtgg gcatgactgg ggtcctgtgg    3660
gtcctgaccc agatgtggcc accccggccg cagtggtctt cattccagga tgcctctttt    3720
ccctcctgat ctattcactg cgttcgccat tcggtcattc ccggggccac cactcccacc    3780
tcaggtgtgt gcttcccttg tgttttatga gatatcccca acccggctgc ttattggccc    3840
cgtccgaggg caggagcata aataagagcc tctgctttgg cgtgggacca ctgtgagctc    3900
cagtcagcgc tgccactgct gagctctggg ccttcgacag gacttggccc cttactgact    3960
tctccgtgtg ctttgggtca tgggtgagga cgcctcctgg caaggctgcg tcctgaggat    4020
taaatcgggt catctgtgaa aactacccag cccagcccct gacactttt tgtttgtttc    4080 ttttagtgac agggtcttgc tctgtcaccc aggctggagt gcagtggtgt gatctcggct    4140
cactcgacct ccggggctca agcaattctc ccacctctgc ctccagagta gctgggacta    4200
taggcacgtg ccaccctgcc aggctaattt cttccatttt ttttagagac agggtctcgc    4260
tatgttcccc aggctgggct caaatggtcc tcccacctca gcctcccaa gtactgggat    4320 tacaggcata agccactgca tctggcctcc atgacacata ttttaaagt ctgattttta    4380 aagtcaaact tttgaagtca gatttaaac ggactatttt gaaaaatata caaaaacgtt    4440
taaaaacaat gaatatccct cacctagaat caataactaa gaatattgac acatttgctt    4500
tggggactgg gcggctggag ctgccatgac aaagctccgc cgaccgagtg gcttttaaac    4560
agagcctgcc ctctcgccga ctgagggctg gacgtgcagg atggagctcc gcagggtcgg    4620
ctcccctgtg ctctgagggg ctctgctcag cctctcccgg ctgtggctta aaaacagagc    4680
ctgtcctccc gccgtgggg gctggacatg caggaccgag gggccacagg gtcggctccc    4740
tgtgctccga gagggctctg ctcagcttct cctggctggg gggttttgtg gccaccctct    4800
gtgttcctgg gttcagaagc atcccccagg ctctgccttc atctctgcac gggtgactct    4860
gtacaggaag ccaggcctgc tggtcaatgg ccacccagcc ctgtgccctc atcttaccta    4920
gtcccagctg ccgtcaccct attcctaata aggccgcctt ctgaggtcat ggggttagga    4980
cttccacata ggaatctgtg gggacacggt tcggcccaca gcccttccca cctccacaca    5040
cacacacgac tgtgaggagt tggaagacct cactcctcac ccctgccagg tcctctaggg    5100
acaagctcgc tgtcctcatc ccagcacagc ccgtgggacg gtttccttgt ccctaatggg    5160
accacggtca gagatgccgg gtctggtctg ggccagcagg ttcctccgcc cggggcaggc    5220
```

```
agccttcttc tgtgcgcttc tggaaagcaa tgtcctgtaa tgcggtctct ctgcgggagc    5280
acccccaccg ccacctcaca ggcctgttcc acagccccgg gatgggctct gtctccctcc    5340
tgaccctgca tagggcacag ccctctctca tcaacccacg atcctacgtg gatccgagag    5400
ggagcacctg gggaaacaat ggaatcccat agaaacaccc caaatctaac ttgatccagg    5460
accagccagt ggtcacttct gaatattcac cttcctagta gacactacca gccaagggag    5520
gccaggaagc cttcctggag gaggtggcct gaggactggg gtgaggcagg ccctgcgtgg    5580
gggtcgccac ccagcacccc cacactgggt gggagccagt ctctgagact ggctggggga    5640
ggtgggagag ggggctgctt gaactgcaga caccgaggtc tagccccac cccacccagc     5700 cagttggtgg aggcagggga ggccgagggg cccagctgga cctgctcccc ggggtggatt    5760
ccaaaatagg ggggttgggg ggggcggaac aggagcccag ggtcctggct tgaggcccag    5820
tggctgaggg ctggtgcaag ccagacagga aaagggttga gcctgtcagc gccagcacag    5880
atcaagtcag gagcaggtcc ctccaccaat gtgtgcaaat aaatagcagc taagtttcca    5940
gttacaagaa caatgcacag atggtcccag ggacattgcg gtgtggacac acagcggcca    6000
ttgtcctgtc gccagcacct cgccctacag ctgggggggtc ccttagcact tcctagccat    6060
gcagggtccc tgctcacagt acccgtgatg acttctgttc ctcacctgcc tgtctgtccc    6120
gacagctgca tggcagccct ggctgggag atggagaccc cgaggggctg cctgcgtgg     6180 tggggcccct gggtcccac tgcattccca gaaacccaga gggcagggca tttcccctgc    6240
tctgtgccga gtccacccag ccccagccta ggcccagtaa gggctgcagc ccaccctgtc    6300
ccaggctgcc tcccaggagc cctcttggcc ctgatgccag aagcccatct tcctccattc    6360
aggcaggtct ctgagtgccc tggcctggct gcctgctggc cctgagagtc acactacccc    6420
acagccctcc ttggtcaaaa tccactctgg agtggctgga agattccccg ggcccacgcc    6480
gcacacgcct atgcagggag cttccctgg ccggccggca gacaagggcg gtctcagaga     6540
gggggctcac ctcagcagcc ccttgtgtag ctggccctcg cccctgccac ctctgggaac    6600
accaccagga agctggggga caggcacgca ggtgaaggag gcgagcgctt gtcagccggg    6660
aggccatggg cacagaggga acagggacac cctgggtggc ctcaaggtca cttcaaaccc    6720
ctcactcgtc ccctgggagg gtgcccagtg aggttggcac taggagttgg tcctggtcac    6780
atgacagacc cacccacctc tggtgtccag ccagcacgcc gtgggccagc ctggctgcag    6840
ggacacgagg gcagcagccc cctcctcctc tgagctggtt gctccttgag tcatcaccac    6900
cgcctgccac ggaggccgcc tgtcccagga agcagaggga ccgcagctgt ggcaaccagg    6960
gcctggtctc tgtgtcacct cgctgggggg ccgtgcccag gcctgagacg gaactgagtg    7020
acagtgcact gggtctgaca gtgtggggct ggcgccatgt ttggggaacc ctgtggcatg    7080
ggacctgtgg gtgagccggg aaaatcaccc cgttgcatgg catctcgggc ctggatctta    7140
agcgcctgtg ttggtgcctc cgcctggcgg aagagccgcg accccacgt tgccatgcgg     7200 gtatcccaag ccctgaccct ggcaggcata tgtttcagga ggtccttgtc ttgggagccc    7260
agggtcgggg gccccgtgtc tgtccacatc cgagtcaatg gcccatctcg tctctgaagc    7320
atctttgctg tgagctctag tccccactgt cttgctggaa aatgtggagg ccccactgcc    7380
cactgcccag ggcagcaatg cccataccac gtggtcccag ctccgagctt gtcctgaaaa    7440
gggggcaaag actggaccct gagcctgcca aggggccaca ctcctcccag ggctggggtc    7500
tccatgggca gccccccacc cacccagacc agttacactc ccctgtgcca gagcagtgca    7560
```

```
gacaggacca ggccaggatg cccaagggtc aggggctggg gatgggtagc ccccaaacag    7620 cccctttctgg gggaactggc ctcaacgggg aaggggggtga aggctcttag taggaaatca    7680
gggagaccca agtcagagcc aggtgctgtg cagaagctgc agcctcacgt agaaggaaga    7740
ggctctgcag tggaggccag tgcccatccc cgggtggcag aggccccagc agagacttct    7800
caatgacatt ccagctgggg tggccctttcc agagcccttg ctgcccgagg atgtgagca    7860 ggtggccggg gaggctttgt ggggccaccc agccccttcc tcacctctct ccatctctca    7920
gactccccag acaggccctg gaaccccccc accttctccc cagccctgct cgtggtgacc    7980
gaaggggaca cgccacctt cacctgcagc ttctccaaca catcggagag cttcgtgcta    8040
aactggtacc gcatgagccc cagcaaccag acggacaagc tggccgcctt ccccgaggac    8100
cgcagccagc ccggccagga ctgccgcttc cgtgtcacac aactgcccaa cgggcgtgac    8160
ttccacatga gcgtggtcag ggcccggcgc aatgacagcg gcacctacct ctgtggggcc    8220
atctccctgg cccccaaggc gcagatcaaa gagagcctgc gggcagagct cagggtgaca    8280
ggtgcggcct cggaggcccc ggggcagggg tgagctgagc cggtcctggg gtgggtgtcc    8340
cctcctgcac aggatcagga gctccagggt cgtagggcag ggaccccca gctccagtcc    8400 agggctctgt cctgcacctg gggaatggtg accggcatct ctgtcctcta gctctggaag    8460 cacccccagcc cctctagtct gccctcaccc ctgaccctga ccctccaccc tgaccccgtc    8520
ctaacccctg acctttgtgc ccttccagag agaagggcag aagtgcccac agcccacccc    8580
agcccctcac ccaggccagc cggccagttc caaaccctgg tggttggtgt cgtgggcggc    8640
ctgctgggca gcctggtgct gctagtctgg gtcctggccg tcatctgctc ccgggccgca    8700
cgaggtaacg tcatcccagc ccctcggcct gccctgccct aaccctgctg gcggccctca    8760
ctcccgcctc cccttcctcc acccttccct caccccaccc cacctccccc catctccccg    8820
ccaggctaag tccctgatga aggcccctgg actaagaccc ccccacctag gagcacggct    8880
cagggtcggc ctggtgaccc caagtgtgtt tctctgcagg acaataggga gccaggcgca    8940
ccggccagcc cctggtgagt ctcactcttt tcctgcatga tccactgtgc cttccttcct    9000
gggtgggcag aggtggaagg acaggctggg accacacggc ctgcaggact cacattctat    9060
tatagccagg acccccacctc cccagccccc aggcagcaac ctcaatccct aaagccatga    9120
tctggggccc cagcccacct gcggtctccg ggggtgcccg gccatgtgt gtgcctgcct    9180 gcggtctcca ggggtgcctg gcccacgcgt gtgcccgcct gcggtctctg ggggtgcccg    9240
gcccacatat gtgcctgcct gcggtctcca ggtgtgcccg gccatgcgt gtgcccacct    9300 gcgagggcgt ggggtgggct tggtcatttc ttatcttaca ttggagacag gagagcttga    9360
aaagtcacat tttggaatcc taaatctgca agaatgccag ggacatttca gagggggaca    9420
ttgagccaga gaggaggggt ggtgtcccca gatcacacag agggcagtgg tgggacagct    9480
cagggtaagc agctcgtagt gggggggccca ggttcggtgc cggtactgca gccaggctgt    9540
ggagccgcgg gcctccttcc tgcggtgggc cgtggggctg actccctctc cctttctcct    9600
caaagaagga ggacccctca gccgtgcctg tgttctctgt ggactatggg gagctggatt    9660
tccagtggcg agagaagacc ccggagcccc cgtgccctg tgtccctgag cagacggagt    9720
atgccaccat tgtctttcct agcggaatgg gcacctcatc cccgcccgc aggggctcag    9780 ccgacggccc tcggagtgcc cagccactga ggcctgagga tggacactgc tcttggcccc    9840
tctgaccggc ttccttggcc accagtgttc tgcagaccct ccaccatgag cccgggtcag    9900
cgcatttcct caggagaagc aggcagggtg caggccattg caggccgtcc aggggctgag    9960
```

-continued

```
ctgcctgggg gcgaccgggg ctccagcctg cacctgcacc aggcacagcc ccaccacagg    10020
actcatgtct caatgcccac agtgagccca ggcagcaggt gtcaccgtcc cctacaggga    10080
gggccagatg cagtcactgc ttcaggtcct gccagcacag agctgcctgc gtccagctcc    10140
ctgaatctct gctgctgctg ctgctgctgc tgctgctgcc tgcggcccgg ggctgaaggc    10200
gccgtggccc tgcctgacgc cccggagcct cctgcctgaa cttgggggct ggttggagat    10260
ggccttggag cagccaaggt gcccctggca gtggcatccc gaaacgccct ggacgcaggg    10320
cccaagactg gcacaggag tgggaggtac atggggctgg ggactcccca ggagttatct     10380
gctccctgca ggcctagaga agtttcaggg aaggtcagaa gagctcctgg ctgtggtggg    10440
cagggcagga aaccccctcca cctttacaca tgcccaggca gcacctcagg cccttttgtgg   10500 ggcagggaag ctgaggcagt aagcgggcag gcagagctgg aggcctttca ggcccagcca    10560
gcactctggc ctcctgccgc cgcattccac cccagcccct cacaccactc gggagaggga    10620
catcctacgg tcccaaggtc aggagggcag ggctggggtt gactcaggcc cctcccagct    10680
gtggccacct gggtgttggg agggcagaag tgcaggcacc tagggccccc catgtgccca    10740
ccctgggagc tctccttgga acccattcct gaaattattt aaaggggttg gccgggctcc    10800
caccagggcc tgggtgggaa ggtacaggcg ttcccccggg gcctagtacc cccgccgtgg    10860
cctatccact cctcacatcc acacactgca cccccactcc tggggcaggg ccaccagcat    10920
ccaggcggcc agcaggcacc tgagtggctg gacaaggga tcccccttcc ctgtggttct     10980
attatattat aattataatt aaatatgaga gcatgctaag gagttctgtc ctgtctggtg    11040
gctgtggggg cagtgggcag gagggaggga ggcctccagg gagggacaag gcggcagcca    11100
ggctgaggct gtgtgtggag ggtgctggtg gctcccctgg atcctggcct gagtcaggcc    11160
ttcccctcgc tgtcccagaa acacacaggc cctcctcgcc ctgtttgccc cactcacatg    11220
tagagccctc cggtgaaaaa ttcctccaac atcacgggc tggggacacc atcttcccca     11280
agcccaggcc ttttaggggg gtcccacggc ccctggccc caggcttcct ggccaggcat     11340
gggtgtccct gagtgactgt gcctgctcca tagcccccgt gtcccatgc ctaccagtcc     11400 ctccgggcag gggtggtacc tggtgccagg gcgtccacag cggggtggga gggctgccct    11460
gggctatgag ggacacagca tctgcgggtc cctccccaag tacacagggt ggggcagcg     11520 ggggaggcgg ggtcacgtct gctggagccc tatcaccctg ctgcggtcct tggcagctag    11580
cagcagggac ggtgcaggga aaggagcct gccaggccct cgggcaccgc agccaaacac     11640
ccactgacac cccggggctc attctctgct tgccatcctg                           11680
```

<210> SEQ ID NO 2
<211> LENGTH: 418
<212> TYPE: DNA
<213> ORGANISM: Homo sapiens

<400> SEQUENCE: 2

```
ggagagtgag gccaaggcct cccccacgga tggtctgaac agggctcggg gagagccctg       60
gaatctgggc agagacccag gcgggcacaa tccccaccca ggaggatcc tggagacaga      120 agaactgtcc tcactcgaac aggtacactt tggatataat gagaaaaata tcaccagctc      180
atctaaactt tgacgtcgta aagccaaggt tagtcccaca tggggctcat cccatcctta      240
ggaaaactcg agtgaggacc aaggatgcct gggcaaggca gagccgccac gcagactccc      300
cacggccaag gtttggggtt ctggccagcc tgacccgtca ttctacagaa acacgcagcc      360
```

```
ccaaggaccg gctgagaggg gacagaggtc ctgcctgccc aggagcaaag agggact        418
```

<210> SEQ ID NO 3
<211> LENGTH: 264
<212> TYPE: DNA
<213> ORGANISM: Homo sapiens

<400> SEQUENCE: 3

```
gcagggtcag gagggagaca gagcccatcc cggggctgtg aacaggcct gtgaggtggc      60
ggtgggggtg ctcccgcaga gagaccgcat tacaggacat tgcttttccag aagcgcacag  120
aagaaggctg cctgccccgg gcggaggaac ctgctggccc agaccagacc cggcatctct   180
gaccgtggtc ccattaggga caaggaaacc gtcccacggg ctgtgctggg atgaggacag   240
cgagcttgtc cctagaggac ctgg                                           264
```

<210> SEQ ID NO 4
<211> LENGTH: 250
<212> TYPE: DNA
<213> ORGANISM: Homo sapiens

<400> SEQUENCE: 4

```
ccagaatctc cagttctgag tcctgagtga cccacgggcc aaccttaaga ggtggcgctg    60
aggcaggaag gcacggccct gacaaggatg ctgcctcagg tgccggggag caggccccgg  120
gagaggggcc gaggtgggga accccccagtc gcctgccaca gtgaagggc accaggaccc   180
ccggggcagg agcctcgagg gggtgtcagg gcggcccag gggtgcccct catcttgtcc    240
tcccagtggt                                                          250
```

<210> SEQ ID NO 5
<211> LENGTH: 499
<212> TYPE: DNA
<213> ORGANISM: Homo sapiens

<400> SEQUENCE: 5

```
cttctggcat cagggccaag agggctcctg ggaggcagcc tgggacaggg tgggctgcag    60
cccttactgg gcctaggctg gggctgggtg gactcggcac agagcagggg aaatgccctg  120
ccctctgggt ttctgggaat gcagtgggga cccagggggcc ccaccaccgc aggcagcccc  180
tcggggtctc catctcccag gccagggctg ccatgcagct gtcggacag acaggcaggt   240
gaggaacaga agtcatcacg ggtactgtga gcagggaccc tgcatggcta ggaagtgcta   300
agggaccccc cagctgtagg gcgaggtgct ggcgacagga caatggccgc tgtgtgtcca   360
caccgcaatg tccctgggac catctgtgca ttgttcttgt aactggaaac ttagctgcta   420
tttatttgca cacattggtg gagggacctg ctcctgactt gatctgtgct ggcgctgaca   480
ggctcaaccc ttttcctgt                                                499
```

<210> SEQ ID NO 6
<211> LENGTH: 28
<212> TYPE: DNA
<213> ORGANISM: Homo sapiens

<400> SEQUENCE: 6

```
gtttagatta gatttggtat ttttgatt                                       28
```

<210> SEQ ID NO 7
<211> LENGTH: 23
<212> TYPE: DNA
<213> ORGANISM: Homo sapiens

```
<400> SEQUENCE: 7
caaatcctct aaaaacaaac tca                                              23

<210> SEQ ID NO 8
<211> LENGTH: 27
<212> TYPE: DNA
<213> ORGANISM: Homo sapiens

<400> SEQUENCE: 8
tcccaacaca acccataaaa caatttc                                          27

<210> SEQ ID NO 9
<211> LENGTH: 25
<212> TYPE: DNA
<213> ORGANISM: Homo sapiens

<400> SEQUENCE: 9
agattagatt cggtattttt gatcg                                            25

<210> SEQ ID NO 10
<211> LENGTH: 23
<212> TYPE: DNA
<213> ORGANISM: Homo sapiens

<400> SEQUENCE: 10
caaatcctct aaaaacaaac tcg                                              23

<210> SEQ ID NO 11
<211> LENGTH: 26
<212> TYPE: DNA
<213> ORGANISM: Homo sapiens

<400> SEQUENCE: 11
cccaacacaa cccgtaaaac gatttc                                           26

<210> SEQ ID NO 12
<211> LENGTH: 264
<212> TYPE: DNA
<213> ORGANISM: Homo sapiens

<400> SEQUENCE: 12
ttaggttttt tagggataag tttgttgttt ttattttagt atagtttgtg ggatggtttt      60
tttgttttta atgggattat ggttagagat gttgggtttg gtttgggtta gtaggttttt    120
ttgtttgggg taggtagttt ttttttgtgt gttttttggaa agtaatgttt tgtaatgtgg   180 ttttttttgtg ggagtatttt tattgttatt ttataggttt gttttatagt tttgggatgg   240
gttttgtttt tttttttgatt ttgt                                          264

<210> SEQ ID NO 13
<211> LENGTH: 264
<212> TYPE: DNA
<213> ORGANISM: Homo sapiens

<400> SEQUENCE: 13
ttaggttttt tagggataag ttcgttgttt ttattttagt atagttcgtg ggacggtttt      60
tttgttttta atgggattac ggttagagat gtcgggtttg gtttgggtta gtaggttttt    120
```

```
tcgttcgggg taggtagttt tttttgtgc gttttggaa agtaatgttt tgtaatgcgg    180
tttttttgcg ggagtatttt tatcgttatt ttataggttt gttttatagt ttcgggatgg    240
gttttgtttt tttttgatt ttgt                                            264
```

PDCD1 AS EPIGENETIC MARKER FOR THE IDENTIFICATION OF IMMUNE CELLS, IN PARTICULAR PD1+ CELLS

CROSS-REFERENCE TO RELATED APPLICATIONS

This application is a 35 U.S.C. § 371 national phase application of International Patent Application No. PCT/EP2018/079184, filed Oct. 24, 2018, which claims priority to German Patent Application No. 102017125019.0, filed Oct. 25, 2017, the entire disclosures of each of which are incorporated herein by reference in their entirety.

The Sequence Listing for this application is labeled "113828.000020 Sequence Listing.txt", which was created on Apr. 21, 2020 and is 20 Kilobytes. The entire content is incorporated herein by reference in its entirety.

The present invention relates to a method, in particular an in vitro method, for identifying PD1+ cells, comprising analyzing epigenetic modifications/properties of (including the methylation status) of at least one CpG position in the mammalian gene region for Progammed cell death 1 (PDCD1), wherein a demethylation or lack of methylation of said gene region is indicative for a PD1+ cell, when compared to a non-PD1+ cell. The analyses according to the invention can identify PD1+ cells on an epigenetic level and distinguish them from all other cells in complex samples, such as, for example, other blood or immune cells. The present invention furthermore provides an improved method for quantifying PD1+ cells, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure PD1+ cells of the blood within any solid organs, tissue or body fluid of a mammal.

BACKGROUND OF THE INVENTION

Commonly, PD1+ cells are defined as cells that actively synthesize the protein encoded by the gene programmed cell death 1. In the current application, PD1+ cells are defined as cells that are rendered capable of expressing PD1 by providing an accessible unmodified primary DNA sequence as shown by the absence of modifications in CpG motifs in the intronic region described and defined in following.

PD1+ cells are cells expressing Programmed cell death protein-1 (PDCD1, also referred to as PD-1). PDCD1 is expressed on a variety of immune cell types, such as activated Thymus-derived lymphocytes (T lymphocytes, T cells), pro-B cells, myeloid-derived dendritic cells, and natural killer (NK) cells. PDCD1 is expressed during a number of different stages of immune development and inflammation, and PDCD1 serves as an important checkpoint receptor involved in immunity regulation and self-tolerance. PDCD1 expression slows the immune response during initial acute antigen recognition by reducing tissue residency and cytokine production, as well as by decreasing the formation of helper cells during the early immune response. Interestingly, PDCD1 promotes apoptosis (programmed cell death) in antigen specific T-cells while simultaneously prohibiting apoptosis in regulatory T cells, which are anti-inflammatory T cells. Thus, PDCD1 is an important regulator of an effective adaptive immune response.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics—heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfate sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

Youngblood et al. (in: Youngblood et al. Chronic virus infection enforces demethylation of the locus that encodes PD-1 in antigen-specific CD8+ T cells. 2011 Sep. 23;35(3): 400-12) disclosed PDCD1 expression to be dependent on methylation of a CpG rich region upstream from the transcription start. This region overlaps with previously identified conserved regions C and B (CR-C & CR-B) of the PDCD1 gene. Methylation of this PDCD1 CpG rich locus inversely correlates with PDCD1 mRNA expression, and is thus involved in regulating immune responses. For example, during differentiation of naïve to effector CD8 T cells in response to an acute infection, the PDCD1 locus is hypomethylated. This event then triggers higher expression of PDCD1 mRNA. When effector CD8 T cells further differentiate into functional memory cells, the PDCD1 locus is being remethylated. Thus, methylation of PDCD1 provides a way of regulating immune responses via PDCD1 expression.

Bally et al. (in: Bally et al. NF-κB regulates PD-1 expression in macrophages. 2015 May 1;194(9):4545-54.) further investigated the methylation state of PDCD1 upstream regions CR-C and CR-B in macrophages. They discovered no changes of methylation of PDCD1 after LPS-stimulation of Bone Marrow-Derived Macrophages (BMDMs).

Goltz et al. (in: Goltz et al. Promoter methylation of the immune checkpoint receptor PD-1 (PDCD1) is an independent prognostic biomarker for biochemical recurrence-free survival in prostate cancer patients following radical prostatectomy. Oncoimmunology. 2016 Sep 2;5(10):e1221555) further demonstrated the methylation state of the PDCD1 upstream locus to be correlated with carcinomas versus normal prostatic epithelium.

In view of the above, it is an object of the present invention to provide an improved and in particular robust method based on DNA-methylation analysis as a superior tool in order to more conveniently and reliably detect, identify, discriminate, and quantify PD1+ cells.

The present invention solves the above object by providing a method for identifying PD1+ cells in a sample, comprising analyzing the methylation status (bisulfite convertibility) of at least one CpG position in the mammalian (e.g. human) gene region for Programmed cell death 1 (PDCD1), wherein preferably said gene region as analyzed is positioned based on/according to SEQ ID No. 1, wherein a demethylation of said gene region is indicative for a PD1+ cell, when compared to a non-PD1+ cell.

The Programmed cell death protein-1 (PDCD1, also referred to as PD-1) belongs in the immunoglobulin superfamily and is a 288 amino acid long cell surface receptor expressed on a variety of immune cell types. Importantly, the formation of a complex between PDCD1 and its ligand Programmed death ligand 1 (PD-L1) or Programmed death ligand 2 (PD-L2) transmits an inhibitory signal that reduces the proliferation and inflammatory activity of cells expressing PDCD1, and thereby suppressing the immune response. Thus, expression of PDCD1 enables the regulated activation and expansion of immune cells, which is necessary for an effective adaptive immune response. The gene for human PDCD1 is found on chromosome 2, 241849881-241858908 reverse strand; Ensembl-ID: ENSG00000188389.

In the context of the present invention, the gene region shall comprise all of the genomic region relating to and encoding for PDCD1. Thus, included are enhancer regions, promoter region(s), introns, exons, and non-coding regions (5'- and/or 3'-regions) that belong to PDCD1. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed.

The present invention is further based on the surprising identification of a region of the PDCD1 gene by the inventors, as specific epigenetic marker, allowing the identification of PD1+ cells as well as the clinical routine application of said analysis.

In the context of the present invention, the genomic region of PDCD1, in particular according to SEQ ID No. 1, more preferably SEQ ID NOs. 2 (Amp 1876), 3 (Amp 1877) or 4 (Amp 1878) allow the identification of PD1+ cells. Surprisingly, the discriminatory pattern of bisulfite convertible and non-convertible cytosine is particularly and even exclusively limited to the genomic region according to SEQ ID No. 1 for PD1+ cells as shown using the amplicon according to SEQ ID No. 1, and in particular in the bisulfite converted sequences according to SEQ ID No. 12 and/or 13 (TpG converted and CpG converted sequences for AMP 1877).

The inventors could demonstrate that in the PD1+ cells the CpG motifs as disclosed are almost completely demethylated (i.e. to more than 70%, preferably 80%, preferably, more than 90% and most preferred more than 95%), whereas the same motifs are completely methylated in PD1— cells.

The differential methylation of the CpG motifs within the aforementioned regions is a valuable tool to identify PD1+ cells, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context.

The assay allows measurement of PD1+ cells without purification or any staining procedures.

Another preferred aspect of the method according to the present invention then further comprises a quantification of the relative amount of PD1+ cells based on comparing relative amounts of said methylation frequency in the region as analyzed with relative amounts of the methylation frequency in a control gene, such as, for example, GAPDH. Said quantification is thus achieved based on the ratio of the bisulfite convertible DNA to non-convertible DNA in the genetic region of PDCD1 (e.g. of SEQ ID No. 1) as described and analyzed herein. Most preferred is a quantification of the relative amount of PD1+ cells is based on an (preferably parallel or simultaneous) analysis of the relative amount of bisulfite convertible DNA of cell-specific region for PDCD1, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID No. 1, preferably oligomers according to any of SEQ ID No. 6 to 11.

In contrast to FACS and mRNA measurements, using the methods according to the present invention, the measurement(s) and analyses can be done independent of purification, storage—and to quite some extent—also to tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the PDCD1 gene region is produced that is a particularly preferred "tool" for performing the method(s) according to the present invention. Consequently, oligomers according to any of SEQ ID No. 6 to 11 or an amplicon as amplified by a primer pair based on SEQ ID No. 6 and 7 or 9 and 10 as mentioned herein constitute preferred embodiments of the present invention. Thus, the sequences of SEQ ID No. 1 to 4 (and, if needed, the complementary sequences thereto) can be used to design primers for amplifications, i.e. serve as "beacons" in the sequence as relevant. Similarly, additional primers and probes can be designed based on the amplicon according to SEQ ID No. 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID No. 1, and is preferably selected from the CpG positions 27, 47, 82, 136, 194, 197, 249, 285, 290, 303, 336, 354, and 369 in the amplicon 1876 according to SEQ ID No. 2, CpG positions 31, 60, 75, 86, 114, 138, 142, 171, 184, 210, 217, and 241 in the amplicon 1877 according to SEQ ID No. 3, CpG positions 35, 56, 74, 104, 118, 130, 150, 182, 196, and 212 in the amplicon 1878 according to SEQ ID No. 4, and is preferably selected from CpG positions 60, 75, 86, 114, 138, 142, 171, 184, 210, 217, and 241 in a fragment of the amplicon 1877 according to SEQ ID No. 3. Preferred are combinations of 3, 4, 5, 6, 7, 8, 9, or 10 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 60, 75, 86, 114, 138, 142, 171, 184, 210, 217, and 241 in the amplicon No. 1877 of the PDCD1 specific bisulfite convertible region (SEQ ID No. 1), or all sites as present on the bisulfite convertible region according to SEQ ID No 1. One or more of positions 60, and/or 138 in AMP 1877 may be excluded.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said PD1+ cells from all major peripheral blood cell types and/or non-blood cells, preferably, but not limited to, cytotoxic T-cells, granulocytes, monocytes, B-cells, CD56++NK cells, T-helper cells, and NKT cells, and other cell types derived from other organs than blood.

In yet another preferred embodiment of the method according to the present invention, the sample is selected from a mammalian body fluid, including human blood samples, or a tissue, organ or a sample of leukocytes or a purified or separated fraction of such tissue, organ or leukocytes or a cell type sample. Preferably, said mammal is a mouse, goat, dog, pig, cat, cow rat, monkey or human. The samples can be suitably pooled, if required.

Another preferred aspect of the method according to the present invention then further comprises the step of concluding on the immune status of said mammal based on said B cells. The B cells can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of PD1+ cells in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said PD1+ cells as e.g. a sample for cell transfer into a patient.

Another preferred aspect of the method according to the present invention then relates to a method as above, further comprising formulating said PD1+ cells as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID No. 6 to 11, or an amplicon according to SEQ ID No. 2 to 5.

Yet another preferred aspect of the present invention then relates to a kit for identifying, quantifying, and/or monitoring PD1+ cells in a mammal based on the analysis of the bisulfite accessibility of CpG positions in the gene region of PDCD1, comprising components for performing a method according to invention as described herein, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID No. 6 to 11.

The present invention also encompasses the use of oligomers or amplicon or a kit according to the present invention for identifying and/or for monitoring PD1+ cells in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma(C$and/or $m C$and/or $hm C$and/or $f C$and/or $cC)$ $b=\Sigma(C$and/or $m C$and/or $hm C$and/or $f C$and/or $cC)$, whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the PDCD1 genetic region and in particular the amplicon as described herein as a marker, the inventors very specifically identified, quantified and particularly differentiated PD1+ cells, and in their relation to other cell types in a sample, for example to other blood cells.

The invention will now be further described in the following examples and with reference to the accompanying figures and the sequence listing, without being limited thereto. For the purposes of the present invention, all references as cited herein are incorporated by reference in their entireties.

FIG. 1 shows the analysis of CpG sites on amplicons No. 1876, 1877, and 1878 (SEQ ID No. 2 to 4, respectively) according to the invention. The horizontal boxes in the table correspond to the CpG positions in the amplicon as analyzed (e.g. CpG 1, 2, etc.) with the positions indicated (AMP1876: 27 corresponding to CpG 1 of Amplicon 1876 . . . etc.), and the columns correspond to the cell types as analyzed.

Figure 2:
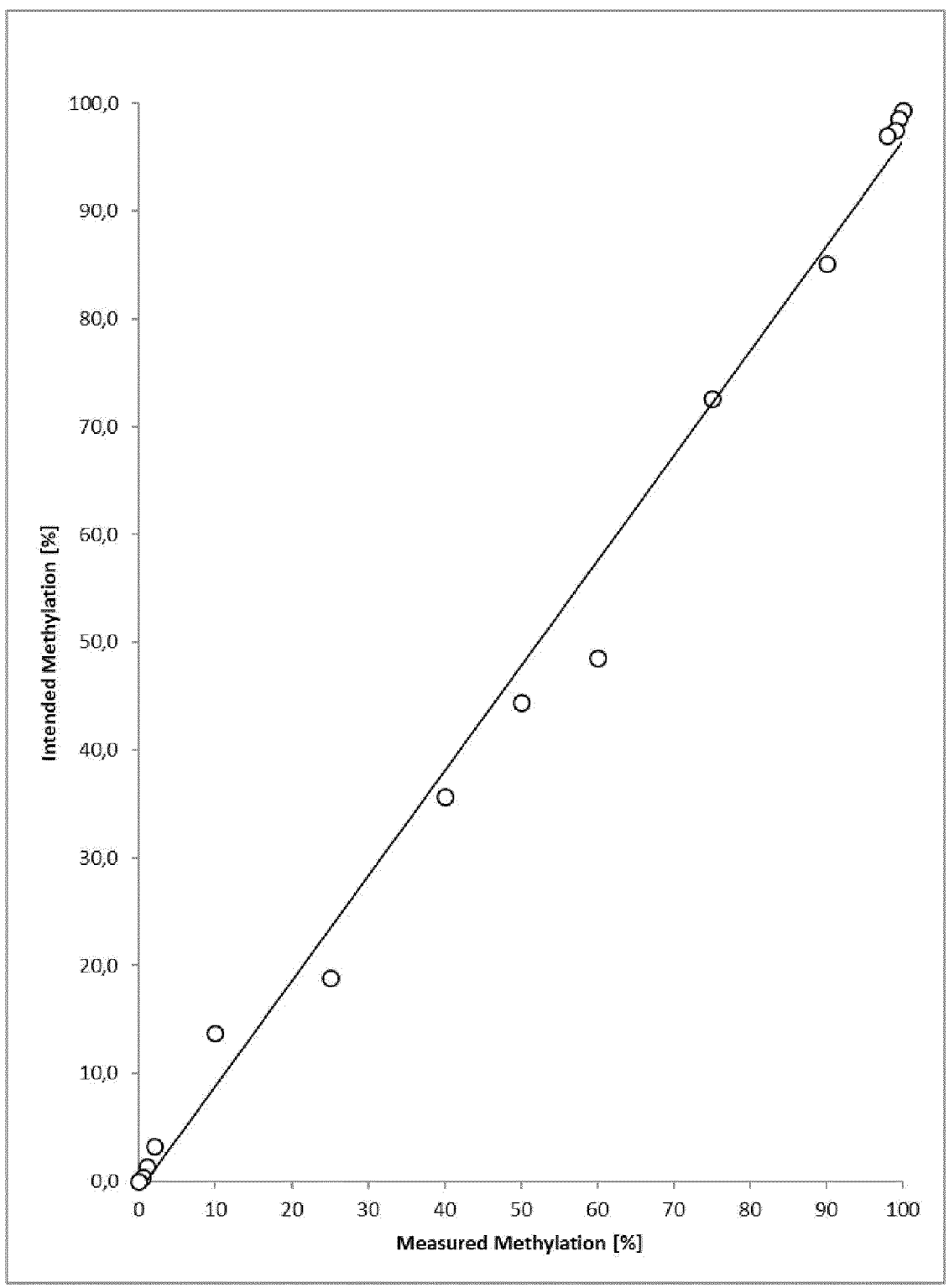

FIG. 2 shows the specificity of the TpG-specific PCR-system according to the invention using test-templates (plasmid-DNA).

FIG. 3A, FIG. 3B, and FIG. 3C show SEQ ID NO: 1, the genomic region of the amplicons according to the present invention, amplicon sequences are underlined.

Figure 4:
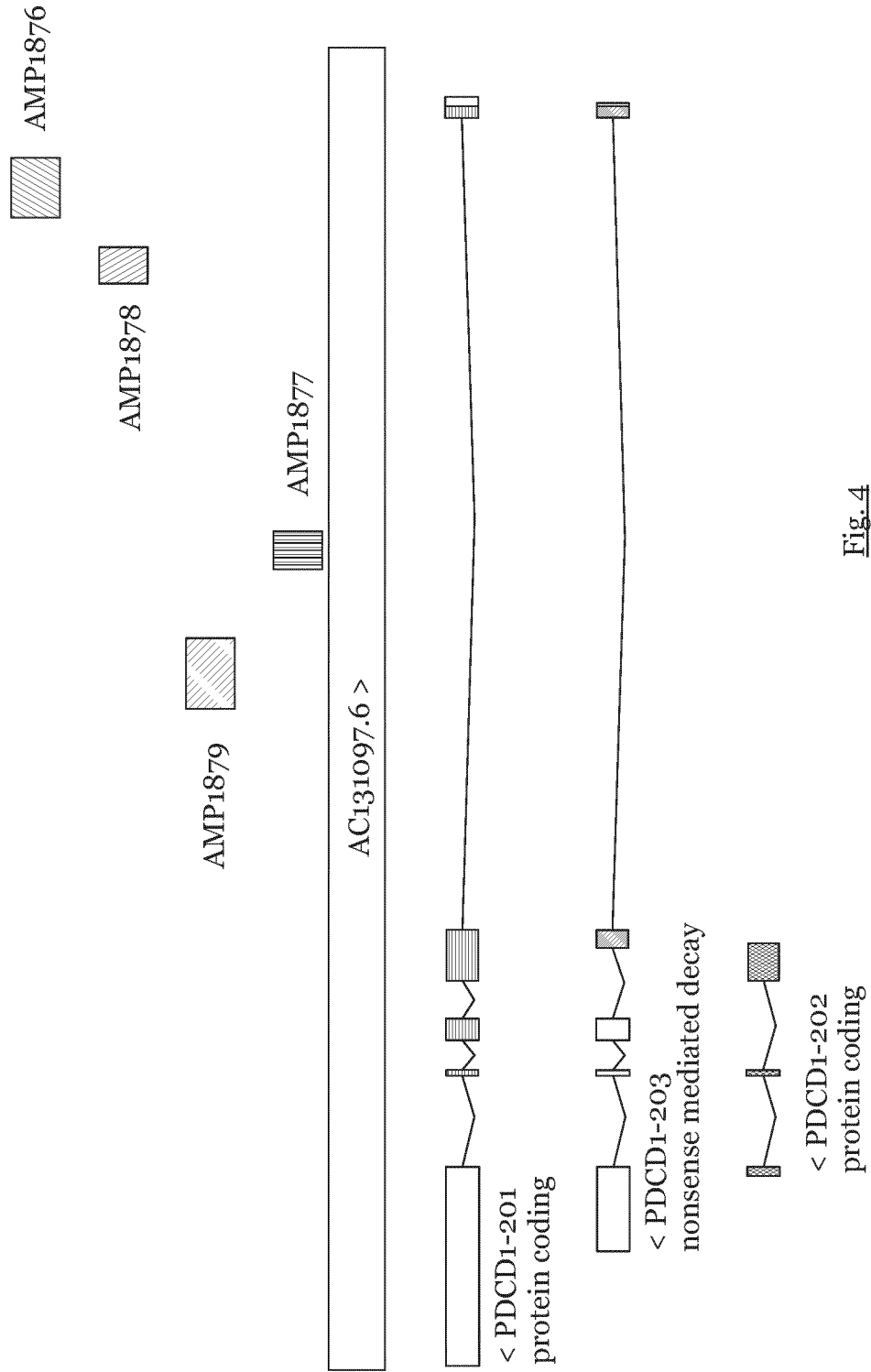

FIG. 4 shows the positions of the amplicons of the invention in the genome.

SEQ ID No. 1 shows the genomic region of the amplicons No. 1876, 1877, 1878, and 1879 according to the present invention (see FIG. 3A, FIG. 3B, and FIG. 3C).

SEQ ID Nos. 2 to 5 show the sequences of amplicons No. 1876, 1877, 1878, and 1879 respectively.

SEQ ID Nos. 6 to 11 show the sequences of specific oligomers (primers and probes) according to the present invention.

SEQ ID Nos. 12 to 13 show the TpG converted and CpG converted sequences, respectively, of the AMP1877 of the invention.

EXAMPLES

Example 1

In order to identify PD1+ cells, qPCR was performed on bisulphite converted samples stemming from the human genomic region according to the sequence SEQ ID No. 1 (see FIG. 3A, FIG. 3B, and FIG. 3C), in particular the regions AMP 1876, AMP 1877, AMP 1878, and AMP 1879 (underlined)

For the actual epigenetic profiling of the amplicon region in blood cell subtypes, the immune cell populations as analyzed were as shown in FIG. 1.

The bisulfate-converted target-regions of preferred qPCR-assay-system as developed were:

```
1877 Primers (qPCR30 FW_T)
                                          (SEQ ID NO: 6)
GTTTAGATTAGATTTGGTATTTTTGATT qPCR30_RV_T
                                          (SEQ ID NO: 7)
CAAATCCTCTAAAAACAAACTCA qPCR30 Probe_T and C:
                                          (SEQ ID NO: 8)
TCCCAACACAACCCATAAAACAATTTC qPCR30_FW_C
                                          (SEQ ID NO: 9)
AGATTAGATTCGGTATTTTTGATCG qPCR30_RV_C
                                          (SEQ ID NO: 10)
CAAATCCTCTAAAAACAAACTCG qPCR30_P_C
                                          (SEQ ID NO: 11)
CCCAACACAACCCGTAAAACGATTTC 1877-TpG converted
                                          (SEQ ID NO: 12)
TTaggtTTtTtagggaTaagTtTgTtgtTTtTatTTTagTaTagTTTgtgg gaTggtttTTttgtTTTtaatgggaTTaTggtTagagatgTTgggtTtggt TtgggTTagTaggttTTtTTgTTTggggTaggTagTTttTtttTtgtgTgTt tTtggaaagTaatgtTTtgtaatgTggtTtTtTtgTgggagTaTTTTTaTT gTTaTTtTaTaggTTtgttTTaTagTTTTgggatgggTtTtgtTtTTTtTT tgaTTTtgT 1877-CpG converted
                                          (SEQ ID NO: 13)
TTaggtTTtTtagggaTaagTtCgTtgtTTtTatTTTagTaTagTTCgtgg gaCggtttTTttgtTTTtaatgggaTTaCggtTagagatgTCgggtTtggt TtgggTTagTaggttTTtTCgTTCggggTaggTagTTttTtttTtgtgCgTt tTtggaaagTaatgtTTtgtaatgCggtTtTtTtgCgggagTaTTTTTaTC gTTaTTtTaTaggTTtgttTTaTagTTTCgggatgggTtTtgtTtTTTtTT tgaTTTtgT
```

The specificity of the TpG-specific PCR-system was demonstrated using test-templates (plasmid-DNA) as shown in FIG. 2.

The cell type specificity (as measured by qPCR) was found as follows (table 1):

| Cell type | Description | Demethylation (%) |
|---|---|---|
| T helper cells | CD3+CD4+ | 4.7 |
| Cytotoxic T cells | CD3+CD8+ | 0.8 |
| NK cells | CD56+ | 0.1 |
| Granulocytes | CD15+ | 0.7 |
| Monocytes | CD14+ | 0.4 |
| B cells | CD19+ | 0.3 |
| TFH cells | CD3+CD4+CXCR5+Bcl+PD1+ | 76.6 |

The invention claimed is:

1. A method for producing an amplicon from a Programmed cell death 1 (PDCD1) gene, the method comprising:
   a) bisulfite treating isolated genomic DNA from a mammalian cell sample to generate bisulfite treated DNA, and
   b) amplifying a region of the PDCD1 gene from the bisulfite treated DNA to produce an amplicon comprising SEQ ID NO: 12.

2. The method according to claim 1, further comprising detecting methylation status of at least one cytosine-phosphate-guanine (CpG) position from the amplicon by a method selected from a methylation specific enzymatic digest, bisulfite sequencing, promoter methylation analysis, CpG island methylation analysis, MSP, HeavyMethyl, MethyLight, Ms-SNuPE, and other methods relying on a detection of amplified DNA.

3. The method according to claim 2, wherein said at least one CpG position is selected from CpG positions 60, 75, 86, 114, 138, 142, 171, 184, 210, 217, and 241 according to SEQ ID NO: 3.

4. The method according to claim 3, further comprising detecting the methylation status of at least two CpG positions selected from CpG positions 60, 75, 86, 114, 138, 142, 171, 184, 210, 217, and 241 according to SEQ ID NO: 3.

5. The method according to claim 1, wherein said sample is selected from a body fluid, a blood sample, a tissue, an organ, a cell type blood sample, or a sample of blood lymphocytes.

6. The method according to claim 1, wherein said method is performed without a step of purifying and/or enriching said cell sample.

7. The method according to claim 1, wherein said mammalian cell sample is from a mammal that suffers from or is likely to suffer from autoimmune diseases, transplant rejections, infection diseases, cancer, and/or allergy.

8. The method of claim 1, wherein the method is performed using a kit comprising:
   a) a bisulfite reagent, and
   b) materials for detecting a bisulfite convertible cytosine at CpG positions in the region from the amplicon.

9. The method of claim 1, wherein the amplifying is performed with a polymerase chain reaction (PCR) using an oligomer comprising the sequence of any one of SEQ ID NOs: 6 to 11.

10. The method according to claim 1, wherein said method is performed using whole blood and/or non-trypsinized tissue.

11. The method of claim 1, wherein the amplifying is performed with a PCR using an oligomer comprising the sequence of SEQ ID NO: 8.

* * * * *